United States Patent [19]

Acott et al.

[11] Patent Number: 5,260,059
[45] Date of Patent: Nov. 9, 1993

[54] TREATMENT OF OPEN-ANGLE GLAUCOMA BY MODULATION MATRIX METALLOPROTEINASES AND THEIR INHIBITOR

[75] Inventors: Ted S. Acott, Newberg; J. Preston Alexander, Forest Grove; John M. B. Bradley, Portland, all of Oreg.

[73] Assignee: The State of Oregon Acting by and through the State Board of Higher Education on Behalf of Oregon Health Sciences University, Portland, Oreg.

[21] Appl. No.: 338,305

[22] Filed: Apr. 14, 1989

[51] Int. Cl.$^5$ ............... A61K 37/54; C12N 9/64
[52] U.S. Cl. ................ 424/94.67; 435/226; 514/913
[58] Field of Search ............ 424/94.67, 94.64; 514/913; 435/226

[56] References Cited

U.S. PATENT DOCUMENTS

| | | | |
|---|---|---|---|
| 3,267,006 | 8/1966 | Hakim et al. | 435/226 |
| 3,677,900 | 7/1972 | Merkel | 424/94.67 |
| 3,869,548 | 5/1975 | Dabis | 424/94.67 |
| 4,174,389 | 11/1979 | Cope | 424/94.67 |

OTHER PUBLICATIONS

Clinical Research, vol. 35, No. 1 (1987), Gard et al., p. 196A.
Sanchez-Lopez, R. et al., *Structure-Function Relationships in the Collagenase Family Member Transin*, J. Biol. Chem. 263, 11892-11899 (Aug. 25, 1988).
Matrisian, L. M. et al., *Isolation of the Oncogene and Epidermal Growth Factor-Induced Transin Gene: Complex Control in Rat Fibroblasts*, Mol. Cell. Biol. 6, 1679-1686 (May, 1986).
Acott, T. S. et al., *Human Trabecular Meshwork Organ Culture: Morphology and Glycosaminoglycan Synthesis*, Investigative Ophthalmology & Visual Science, 29, 90-100 (Jan., 1988).
Acott, T. S. et al., *Trabecular Meshwork Glycosaminoglycans in Human and Cynomolgus Monkey Eye*, Investigative Ophthalomology & Visual Science, 26, 1320-1329 (Oct., 1985).
Stetler-Stevenson, W. G. et al., *The Activation of Human Type IV Collagenase Proenzyme*, J. Biol. Chem. 264, 1353-1356 (Jan. 25, 1989).
Mainardi, C. L. et al., *Degradation of Type IV (Basement Membrane) Collagen by a Proteinase Isolated from Human Polymorphonuclear Leukocyte Granules*, J. Biol. Chem. 255, 5435-5541 (Jun. 10, 1980).
Collier, I. E., *H-ras Oncogene-transformed Human Bronchial Epithelial Cells (TBE-1) Secrete a Single Metalloprotease Capable of Degrading Basement Membrane Collagen*, J. Biol. Chem. 263, 6579-6597 (May 15, 1988).
Murphy, G. et al., *Metalloproteinases from rabbit bone culture medium degrade types IV and V collagens, laminin and fibronectin*, Biochem J. 199, 807-811 (1981).
Liotta, L. A. et al., *Partial Purification and Characterization of a Neutral Protease Which Cleaves Type IV Collagen*, Biochem., (published 1981 by American Chemical Society).
Hibbs, M. S. et al., *Biochemical and Immunological Characterization of the Secreted Forms of Human Neutrophil Gelatinase*, J. Biol. Chem. 260, 2493-2500 (Feb. 25, 1985).

(List continued on next page.)

Primary Examiner—Jacqueline Stone
Attorney, Agent, or Firm—Klarquist, Sparkman, Campbell, Leigh & Whinston

[57] ABSTRACT

A method of treating open-angle glaucoma consisting of providing to the trabecular meshwork a substance such as MMP-1, MMP-2, MMP-3, basic heparin-binding growth factor, nerve growth factor, Interleukin-1, Interleukin-6, TPA, $Ca^{++}$, $Zn^{++}$, plasmin, trypsin, and APMA in effective amount to lower intraocular pressure is provided. A method of treating retinal disease such as; retinal degeneration, ocular neovascularization, and diabetic retinopathy consisting of providing to the optic cup a TIMP, retinoic acid, Razoxane, EDTA, EGTA or 1,10-phenanthrolie in an effective amount to ameliorate the retinal disease is also provided.

5 Claims, No Drawings

OTHER PUBLICATIONS

Chin, J. R. et al., *Stromelysin, a Connective Tissue-degrading Metalloendopeptidase Secreted by Stimulated Rabbit Synovial Fibroblasts in Parallel with Collagenase*, J. Biol. Chem. 260, 12367–12376 (Oct. 5, 1985).

Wilhelm, S. M. et al., *Human skin fibroblast stromelysin: Structure, glycosylation, substrate specificity, and differential expression in normal and tumorigenic cells*, Proc. Natl. Acad. Sci. USA, 84, 6725–6729 (Oct., 1987).

Okada, Y. et al., *A Metalloproteinase from Human Rheumatoid Synovial Fibroblasts that Digests Connectiver Tissue Matrix Components*, J. Biol. Chem. 261, 14245–14255 (Oct. 25, 1986).

Whitham, S. E. et al., *Comparison of human stromelysin and collagenase bycloning and sequence analysis*, Biochem. J. (1986) 240, 913–916 (U.K.).

Herron, G. S. et al., *Secretion of Metalloproteinases by Stimulated Capillary Endothelial Cells*, J. Biol. Chem. 261, 2810–2813 (Feb. 25, 1986).

Frisch, S. M. et al., *Coordinate regulation of stromelysin and collagenase genes determined with cDNA probes*, Proc. Natl. Sci. USA, 84, 2600–2604 (May, 1987).

Stricklin, G. P. et al., *Human Skin Fibroblast Procollagenase: Mechanisms of Activation by Organomercurials and Trypsin*, Biochem., 22, 61–68 (1983).

Gordon, J. M. et al., *Collagenase in Human Cornea*, Arch. Ophthalmol., 98, 341–345 (Feb., 1980).

Stricklin, G. P., *Human Skin Fibroclast Collagenase: Chemical Properties of Precursor and Active Forms*, Biochem., 17, 2331–2337 (1978).

Goldberg, G. I. et al., *Human Fibroblast Collegenase*, J. Biol. Chem. 261, 6600–6605 (May 15, 1986).

Hasty, K. A. et al., *The Collagen Substrate Specificity of Human Neutrophil Collagenase*, J. Biol. Chem. 262, 10048–10052 (Jul. 25, 1987).

Birkedal-Hansen, H., *Catabolism and Turnover of Collagens: Collagenases*, Methods in Enzymology, 144, 140–171, 259 (1987).

Johnson-Muller, B. et al., *Regulation of corenal collagenase production: Epithelial-stromal cell interactions*, Proc. Natl. Acad. Sci. USA, 75, 4417–4421 (Sep. 1978).

Johnson-Wint, B., *Regulation of stromal cell collagenase production in adult rabbit cornea: In vitro stimulation and inhibition by epithelial cell products*, Proc. Natl. Acad. Sci. USA, 77, 5331–5335 (Sep. 1980).

Berman, M. B. et al., *Regulation of Collagenase Activity in the Ulcerating Cornea by Cyclic-AMP*, Exp. Eye Res. 22, 209–218 (1976).

Vadillo-Ortega, F. et al., *A Latent Collagenase in Human Aqueous Humor*, Investigative Ophthalmology & Visual Science, 30, 332–335 (Feb. 1989).

Reynolds, J. J. et al., *Tissue metallo-proteinase inhibitors and their role in matrix catabolism*, Cellular Interactions, Chapter 16, 205–213.

Campbell, E. J. et al., *Monocyte Procollagenase and Tissue Inhibitor of Metalloproteinases*, J. Biol. Chem. 262, 15862–15868 (Nov. 25, 1987).

Herron, G. S. et al., *Secretion of Metalloproteinases by Stimulated Capillary Endothelial Cells*, J. Biol. Chem. 261, 2814–2818 (Feb. 25, 1986).

Docherty, A. J. P. et al., *Sequence of human tissue inhibitor of metalloproteinases and its identity to erythroid-potentiating activity*, Nature 318, 66–69 (Nov. 7, 1985).

Patent Cooperation Treaty International Search Report dated Aug. 14, 1990.

Mittag, et al., "Phorbal ester: effect on intraocular pressure, adenylate cyclase, and protein kinase in the rabbit eye," Chemical Abstracts, 108:70455Z (1988).

Duncan, et al., "The effects of Razoxane (ICRF 159) on the production of collagenase and inhibitor (TIMP) by stimulated rabbit articular chondrocytes," Biochemical Pharmacology, 32(24):3853–3858 (1983).

TREATMENT OF OPEN-ANGLE GLAUCOMA BY MODULATION MATRIX METALLOPROTEINASES AND THEIR INHIBITOR

ACKNOWLEDGEMENT OF GOVERNMENT SUPPORT

This invention was made with government support under NIH Grant EY-03279, awarded by the National Institutes of Health. The government has certain rights in the invention.

FIELD OF THE INVENTION

This invention relates to a method of treating ocular disease by modulating cellular secretion of a family of matrix metalloproteinases and their inhibitor. Specifically, differential stimulation of secretion of interstitial collagenase, gelatinase or type IV collagenase, stromelysin or proteoglycanase, and their tissue glycoprotein inhibitor is employed to treat open-angle glaucoma, retinal degeneration and detachment, ocular neovascularization and diabetic retinopathy.

BACKGROUND OF THE INVENTION

Mammalian extracellular matrix (ECM) turnover is though to be initiated by the secretion of several proteinases, which cause partial degradation of specific matrix components. Thereafter, the disrupted matrix components are taken up and degraded further within lysosomal vesicles. Interstitial collagenase, gelatinase or type IV collagenase, and stromelysin or proteoglycanase are members of a family of matrix metalloproteinases with sufficient diversity in substrate specificities to achieve this initial disruption. These metalloproteinases are active at neutral pH and are known to be secreted by a variety of different cell types.

Interstitial collagenase (MMP-1), also called type I-II-III collagenase is an endopeptidase capable of cleaving each of the α-chains of the collagen triple helix at a Gly-Ile or Gly-Leu site located about one-fourth the distance from the carboxy-terminus. This produces thermally unstable soluble fragments about one-fourth and three-fourths the original size, which in turn are susceptible to degradation by gelatinases. Hasty et al., *J. Biol. Chem.* 262, 10048-10052 (1987) report immunologically distinct interstitial collagenases from fibroblasts and neutrophils. The latter has a higher catalytic rate toward Type I collagen, while the former is more active toward Type III collagen. Goldberg et al., *J. Biol. Chem.* 261, 6600-6605 (1986) report that there are two forms of interstitial collagenase produced by human skin fibroblasts—one, an unmodified procollagenase, $Mr \approx 52$ kDa, and the other, a glycosidated form, $Mr \approx 57$ kDa. None of these interstitial collagenases appear capable of degrading Type IV or V collagen.

Ocular tissues have been shown to secrete interstitial collagenase, and the secretion has been shown to be controlled by various extracellular factors. Johnson-Wint *Proc. Natl. Acad. Sci. USA* 77, 5331-5335 (1980) demonstrated that cornea stromal cell collagenase production is regulated by stimulators and inhibitors secreted by corneal epithelial cells. In an earlier report Johnson-Muller et al., *Pro. Natl. Acad. Sci. USA* 75, 4417-4421 (1978) described other soluble chemical and biological agents capable of stimulating macrophages to secrete collagenase. These include: neutral proteases, prostaglandins, bacterial endotoxins, colchicine, phorbol myristic acid, and cytochalasin B. Others (Berman et al., *Exp. Eye Res.* 22, 209-218 (1976)) have described regulation of collagenase activity in corneal tissue by cyclic-AMP.

Gelatinase (MMP-2) or Type IV collagenase is a neutral metalloproteinase capable of hydrolyzing basement membrane type IV collagen into the characteristic ¼ amino-terminal ¾ carboxyl-terminal fragments. The protein is secreted by a variety of cells, for example fibroblasts and tumor cells, as a 70 kDa Type IV procollagenase. This latent proenzyme is converted to a 62 kDa Type IV collagenolytically active enzyme by the autocatylitic removal of an 80 residue peptide fragment from the amino terminus (Stetler-Stevenson et al., *J. Biol. Chem.* 264, 1353-1356 (1989). In addition to Type IV collagenolytic activity, gelatinase has been reported to have activity toward gelatin (degraded Type I, II and III collagen), Type V and Type VII collagen, fibronectin, and laminin. (See for example, Murphy et al., *J. Biol. Chem.* 199, 807-811 (1981)). This enzyme is known to be inhibited by EDTA and 1,10-phenanthroline, and to require Zn and/or Ca for its activity. Hibbs et al., *J. Biol. Chem.* 260, 2493-2500 (1985) has demonstrated the enzyme to be rapidly secreted from neutrophils stimulated with phorbol myristate acetate (TPA).

Stromelysin (MMP-3) is a neutral metalloendopeptidase secreted by various cell types. This enzyme has been reported to have a 55% homology with interstitial collagenase. Chin et al., *J. Biol. Chem.* 260, 12367-12376 (1985) demonstrated that rabbit synovial fibroblasts induced by agents such as TPA, Cytochalasin B, and poly-(2-hydroxyethyl methacrylate) secrete prostromelysin, Mr=51 kDa. This metal (Zn, Ca) dependent proteinase was activated by trypsin and 4-aminophenolmercuric acetate (AMPA) to a $Mr \approx 41$ kDa form with activity toward casein, cartilage proteoglycans, $\alpha_1$-proteinase inhibitor, immunoglobulin G2a, fibronectin, laminin, and Type IV collagen. In addition to being inhibited by metal chelators such as EDTA and 1,10-phenanthroline, the enzyme is normally secreted from endothelial cells complexed with tissue inhibitor of metalloproteinases (TIMP), Herron et al., *J. Biol. Chem.* 261, 2810-2813 (1986). The complete sequence of human skin fibroblast stromelysin has been determined by Wilhelm, et al., *Proc. Natl. Acad. Sci. USA* 84, 6725-6729 (1987). These authors demonstrated great homology between human stromelysin and rat transin, an oncogene transformation-induced protein. The induction of transin transcription by various oncogenes and epidermal growth factor (EGF) was described by Matrisian et al., *Mol. Cell. Biol.* 6, (1986). Other transforming factors shown to induce stromelysin in human fibroblasts include tumorgenic agents such as u.v. light, mitomycin-c, and interleukin-1 (IL-1). Whitham, et al., *J. Biol. Chem.* 240, 913-916 (1986).

The members of the foregoing family of matrix metalloproteinases share many structural and functional similarities, including inhibition by an endogenous inhibitor, tissue inhibitor of metalloproteinase (TIMP). TIMP from human amniotic fluid and cultured fetal lung fibroblasts has been sequenced, and was reported to be immunologically identical to a variety of forms of the protein found in other tissues or body fluids, these inhibitors range in size from $Mr \approx 20-28$ kDa. It appears that a variety of cells coordinate synthesis of MMP-1, MMP-2 and MMA-3 with their specific inhibitor TIMP in vivo (Herron et al., *J. Biol. Chem.* 261, 2814–2818 (1986)).

A variety of agents are known to stimulate secretion of both MMPs and TIMP from various cells; however, few are known to do so differentially. One exception, reported by Duncan et al., *Biochemical Pharmacology* 32, 3853–3858 (1983) is Razoxane, which inhibited collagenase production and stimulated TIMP production.

The existence of these metalloproteinases and their inhibitor in ocular tissue, other than cornea and sclera, has not been demonstrated. Furthermore, the relationship of these secreted proteins to ocular disease, especially glaucoma and retinal disease, has not been ascertained.

SUMMARY OF THE INVENTION

A method of treating open-angle glaucoma is provided. The method comprises providing to the trabecular meshwork, by site specific delivery means, an extracellular matrix metalloproteinase/tissue inhibitor (MMP/TIMP) ratio modulating substance in an effective amount to reduce intraocular pressure. The modulating substance is capable of increasing the MMP/TIMP ratio, and the preferred method of delivery is by microinjection. The site of delivery is to the trabecular meshwork or tissue in direct fluid communication therewith (i.e., the aqueous humor). Preferred modulating substances include MMP-1, MMP-2, MMP-3 per se, basic or acidic heparin-binding growth factor, nerve growth factor, Interleukin-1, Interleukin-6, 12-O-tetradecanolphorbol 13-acetate (TPA), Ca ion, Zn ion, plasmin, trypsin, 4-aminophenolmercuric acetate (APMA) and combinations thereof. Most preferred modulating substances include matrix metalloproteinases (collagenase, gelatinase, stromelysin, and transin) pro-matrix metalloproteinases (procollagenase, progelatinase, prostromelysin, and protransin) and collagenolytically active fragments thereof.

The invention also provides a method of treating retinal disease, specifically retinal degeneration or detachment, diabetic retinopathy and ocular-neovascularization. The method comprises providing to the optic cup (retina, and retinal pigmented epithelium) or tissue in direct fluid communication therewith (e.g., choroid, posterior vitreous), by site specific delivery means (e.g., microinjection), an extracellular matrix metalloproteinase/tissue inhibitor (MMP/TIMP) ratio modulating substance in an effective amount to ameliorate the retinal disease.

In this embodiment of the invention, it is preferred that the modulating substance decrease the MMP/TIMP ratio, and be selected from the group; TIMP (natural or recombinant) retinoic acid, Razoxane, Dexamethasone, EDTA, EGTA, 1,10-phenanthroline, and combinations thereof.

DETAILED DESCRIPTION OF THE INVENTION

It has been discovered that certain ocular diseases can be treated by providing to the diseased tissue, or tissue in fluid communication therewith, a matrix metalloproteinase/tissue inhibitor (MMP/TIMP) ratio modulating substance. The MMP/TIMP ratio modulating substance is selected to adjust the MMP/TIMP ratio in a particular direction depending on the ocular disease to be treated. It has been found that by increasing the MMP/TIMP ratio in the trabecular meshwork, intraocular pressure can be reduced, ameliorating the symptoms of open-angle glaucoma. Conversely, decreasing the MMP/TIMP ratio in the retina is effective in treating retinal degeneration or detachment, and diabetic retinopathy and the attendant ocular neovascularization. Accordingly, since the direction of modulation will be different depending on the ocular disease, it is important to provide or direct the selected MMP/TIMP ratio modulating substance directly to the diseased tissue instead of systemically.

GLAUCOMA AND INTRAOCULAR PRESSURE

The intraocular pressure in the normal human aqueous and vitreous is about 15 to 16 mmHg, with a diurnal variation of about 5 mmHg or more. Many people have intraocular pressures greater than the accepted safe range, but without significant angle closure or optic cup changes which would contra-indicate therapeutic intervention. At higher pressures, i.e., 25–40 mmHg, the risk of vision loss makes treatment an over-riding necessity regardless of anatomical considerations. Consequently, there are certain intraocular pressures either alone or in combination with angle closure which would indicate treatment to avoid visual loss. Since neither the pathological or target intraocular pressure can be determined with precision, due to individual variations in sensitivity, initiation and cessation of treatment or therapy in accordance with the present invention is carried out at the discretion of the opthamologist.

Three basic causes of increased intraocular pressure are: (1) stenosis or blockage of the aqueous outflow channels through the trabecular meshwork and canal of Schlemm; (2) increased venous pressure in the head region, causing secondary ocular hypertension; and, (3) increased production of aqueous in the ciliary processes. The incidence of (1), where no clear anatomical variance is detectable is much higher than (2) or (3) and therefore, is of primary interest. Various prior art treatments have been directed at (2) and (3) above. The instant invention is directed at alleviating blockage or clogging of the trabecular meshwork by increasing the rate of remodeling and repair of the extracellular trabecular matrix. It has been discovered that the rate of remodeling and repair is controlled by the trabecular cells, and that these cells exert their control by secreting a family of matrix metalloproteinases including MMP-1, MMP-2, MMP-3, and transin, as well as their glycoprotein tissue inhibitor, TIMP.

Briefly, it has been discovered that human trabecular explants and human and fetal calf trabecular cells in culture secrete four major gelatinases at approximate $Mr \approx 110, 67, 60,$ and $224$ kDa, in order from highest to lowest activity toward their substrate, gelatin. Minor gelatinases are observed in SDS-PAGE gels at 170, 215, 92, 47, and 270 kDa. Caseinases of approximate $Mr \approx 67$, 61, 110, and 73 kDa are also secreted in order from highest to lowest activity. Treatment with the mitogen TPA dramatically increases the secretion of trabecular gelatinase at 110 kDa and 67 kDa, and significantly increases secretion of the 60 kDa and 224 kDa gelatinases. The above enumerated trabecular caseinases were also observed to increase with TPA treatment. In contrast, TPA treatment of corneal endothelial cells increases gelatinase secretion only slightly, if at all, and has no effect on the secretion of scleral gelatinases.

Fifteen samples of aqueous humor were analyzed similarly for the presence of MMPs. All samples contained from two to five gelatinases and one or two caseinases. The major gelatinase was at 67 k and the major casinase was at 86 k. Minor gelatinases were seen consistently at 185 k and occasionally at 53 k and >300 k; a minor caseinase was observed at 69 k. Aqueous from two aphakic donors contained a gelatinase of 110 k. Aqueous MMPs in normal and inflamed human or cat eyes were not different.

From these and other studies it was found that it is the MMP/TIMP ratio that determines the rate of remodeling and repair. Substances which increase the MMP/TIMP ratio increase the rate of remodeling, while substances which decrease the ratio decrease the rate of remodeling. It has also been found that increasing the remodeling rate increases the aqueous humor outflow rate which, in turn, lowers the intraocular pressure. It is thought that, as the trabecular extracellular matrix is degraded and removed, cellular debris and other blocking agents are concomitantly removed. Additionally, it is believed that by increasing the rate of degradation of the matrix of those components of the matrix which are more slowly synthesized, i.e., the glycosaminoglycans, particularly in the narrow regions of the meshwork such as the juxtacanalicum, improved aqueous outflow is achieved.

A variety of substances have been identified which are effective in increasing the MMP/TIMP ratio and therefore increasing the remodeling rate of the trabecular meshwork.

Increasing the rate of synthesis and secretion of the pro-MMPs intrabercular cells with growth factors such as; basic heparin-binding growth factor, nerve growth factor (NGF), and epidermal growth factor (EGF) has been found to differentially increase MMP secretion over TIMP. Similary, tumor promoters such as the mitogen TPA (Sigma) and mitomycin-c (Sigma) and cytokines such as Interleukin-1 (IL-1) and Interleukin-6 (IL-6) (both from R&D Systems) are effective increasing the rate of synthesis of MMPs in human corneoscleral explants. EGF and NGF are obtained from Boehringer-Mannheim.

Activation or conversion of pro-MMPs to their active form is an alternative way of effectively increasing the MMP/TIMP ratio. Activators such as plasmin, trypsin, and APMA can be used either in vivo or in vitro to convert pro-MMPs to their active form. $Ca^{++}$ and $Zn^{++}$ can also be added to fully activate either the pro or core metalloproteinase. The term "Pro-MMPs" as used herein is used to mean procollagenase, progelatinase, prostromelysin, protransin, and other members of the metalloproteinases secreted by trabecular cells. Plasmin (fibrolysin) trypsin and APMA used in conjunction with the instant invention are commercially available (e.g., Sigma-Aldrich).

Alternatively, the MMP/TIMP ratio can be increased by simply adding exogenous MMPs, pro-MMPs or collagenolytically active fragments thereof directly to the anterior aqueous chamber or trabecular meshwork. Either natural or recombinant MMPs or pro-MMPs, either singly or in combination, can be added. It is preferred that when pro-MMPs are added they are preceded or succeeded with an activator (e.g., trypsin) as described above.

The MMP/TIMP ratio modulating substances used in conjunction with the instant invention can be obtained from commercial sources or prepared by procedures set forth in the scientific literature. For example, collagenase is available from commercial sources (e.g., Sigma) or can be prepared from skin fibroblasts (ATCC CRL-1224) as described by Stricklin et al., *Biochemistry* 22, 61–68 (1983) or from neutrophilis as described by Hasty et al. *J. Biol. Chem.* 262, 10048–10052 (1987). Gelatinase is also available from commercial sources (e.g., Sigma or Worthington Biochemicals) or can be prepared as described by Stetler-Stevenson et al. *J. Biol. Chem.* 264, 1353–1356 (1989), Murphy et al., *Biochem J.* 199, 807–811 (1981), Collier et al., *J. Biol. Chem.* 263, 6579–6587 (1988), or Hibbs et al. *J. Biol. Chem.* 260, 2493–2500 (1985). Stromelysin is prepared from synovial fibroblasts as described by Okada et al. *J. Biol. Chem.* 261, 14245–14255 (1986) or from skin fibroblasts as described by Whitham et al., *Biochem. J.* 240, 913–916 (1986). These references are herein incorporated by reference. Alternatively, any or all can be prepared in recombinant form, by expressing cDNA's or RNAs in microbial, mammalian, or in vitro systems (see for example ICN, Promega, or Stratagene systems and kits).

Any of the above described MMP/TIMP ratio modulating substances can be employed separately or in combination with one another or with other traditional therapies including laser trabeculoplasty (LTP).

In examining the effects of various growth factors in combination with LTP it was found that LTP alone on human corneoscleral organ culture explants causes the release of a factor that induces trabecular cell division at sites remote from the actual burn region. Human corneoscleral organ culture explants used in these studies were prepared and maintained as previously described; Acott et al. *Invest. Ophthalmol. Vis. Sci.* 26, 1320–1329 (1985) and Acott et al. *Invest Ophthalmol. Vis. Sci.* 29, 90–100 (1988) both incorporated herein by reference. Using oligonucleotide and cDNA probes to measure changes in the levels of mRNAs for MMPs it has been discovered that these mRNA levels increase to a maximum by about 8 hours and decline to baseline levels by 24 hours post LTP. Media removed from LTP-treated explants, after being conditioned for 8 hours, produced the same temporal changes in these mRNA levels when it was applied to untreated explants. Therefore, a media-borne signal is released by LTP-treatment which mediates trabecular responses. Passage of the media through a heparin-Sepharose (Pharmacia) column before adding it to the untreated explants, eliminates their 8 hour response, suggesting that it may be due at least in part to a basic heparin-binding growth factor.

The MMP/TIMP ratio modulating substances used to treat open-angle glaucoma are delivered directly to the trabecular meshwork or tissue in fluid communication therewith instead of systemically. This is desirable becuase the collagenolytic activity caused by increasing the MMP/TIMP at the "wrong site" could lead to undersirable matrix degradation causing neovascularization and retinal degradation as described below. Accordingly, MMP/TIMP ratio modulating substances are normally delivered directly to the trabecular meshwork or the anterior aqueous chamber. By way of example, this delivery can be accomplished with topical solutions (eye drops) added directly or in conjunction with a transdermal carrier. Alternatively, these ratio modulating substances can be delivered directly by microinjection or equivalent means.

In an alternative embodiment, these substances can be delivered conjugated to polyclonal antibodies (see, for example, Stricklin et al. *Biochemistry* 17, 2331–2337 (1978)) monoclonal antibodies (e.g., mouse monoclonal antibodies to human EGF receptors commercially available from Oncogene Science) or biologically active fragments thereof. These ratio modulating substances are conjugated to antibodies with homo- or heterobifunctional linking agents commercially available from, for example, Pierce (see 1988 Handbook and General Catalog). Additionally, these ratio modulating substances may be linked through a linkage susceptible to cleavage by, for example, Proteinases, esterases, reducing agents, e.g., N-Succinimidyl 3-(2-pyridyldithio)-propionate, or light.

RETINAL DEGRADATION

As previously described, retinal disease, including diabetic retinopathy, ocular neovascularization, and retinal degradation or detachment is treated according to the present invention by providing to the optic cup (i.e. retina or retinal pigmented epithelium (RPE) or tissue in direct fluid communication therewith (e.g., choroid or posterior vitreous humor) a MMP/TIMP ratio modulating substance in an effective amount to ameliorate the retinal disease. As set forth in greater detail in Example I below, it has been discovered that RPE cells secrete both MMPs and TIMP. Briefly, several proteinases have been identified, by SDS-PAGE, that are secreted by retinal pigmented epithelial (RPE) cells in culture. Three gelatinases predominate with approximate $Mr \approx 67$ k, 110 k, and 59 k in order from highest to lowest activity. Two bands at 40 k and 45 k are also present in lower activities and in some but not all cell lines a pair of bands can be seen at 185 k and 200 k. Three caseinases with approximate $Mr \approx 76$ k, 53 k, and 130 k are detected, listed from highest to lowest activities. Prolonged pretreatment produces additional bands that appear to be degradation products of the larger bands.

Under reducing conditions, immunoblots of western transfers show three collagenases at $Mr \approx 67$ k, 59 k, and >280 k, two gelatinases at $Mr \approx 67$ k and 224 k and TIMP at $Mr \approx 35$ k and 170 k. In tube assays for the MMPs, low activity suggests that TIMPs are secreted at ratios which regulate these enzymes activities.

Treatment of RPE cultures with the mitogen TPA induces unequal increases in the secretion of gelatinases with $Mr \approx 67$ k, 110 k, 45 k 40 k and to a much lesser extent the 59 k band. The 200 k and 185 k bands are not affected. Secretion of 130 k and 53 k caseinases is also increased dramatically by TPA but the 76 k band is not. These matrix metalloproteinases and their TIMPs play an important role in the function and pathology of the RPE. It has further been discovered that by decreasing the MMP/TIMP ratio, i.e., increasing the amount of TIMP relative to MMP, ocular diseases such as those described above can be effectively treated.

A number of substances have been identified which are effective in ameliorating these retinal diseases. Those substances include chelators such as Razoxane, Dexamethasone, EDTA, EGTA, and 1,10-phenanthroline. Alternatively, retinoic acid has been found to be suitable for use in accordance with the present invention. In an alternative embodiment, the MMP/TIMP ratio is decreased by adding exogenous TIMP either isolated from natural sources (Reynolds et al. *Research Monographs in Cell and Tissue Physiology* 6, 205-213, Dingle and Gordon Eds. Elsevier/North-Holland Biomedical Press New York (1981)) or prepared by recombinant techniques; Docherty et al. *Nature* 318, 66-69 (1985).

As described above for the treatment of glaucoma, it is necessary to deliver the MMP/TIMP ratio modulating substance directly to the retina or tissue in fluid communication therewith to avoid inducing or exacerbating other ocular diseases such as ocular hypertension at other sites in the eye. Accordingly, substances capable of reducing the MMP/TIMP ratio in the retina are provided by site specific means such as microinjection to the choroid, RPE, or posterior vitreous. Alternatively, as discussed above, these ratio lowering substances can be delivered conjugated to polyclonal or monoclonal antibodies or fragments thereof.

The following examples are included to assist one of oridinary skill in making and using the invention. They are intended as representative examples only and are not intended in any way to limit the scope of this disclosure or the scope of protection granted by Letters Patent hereon.

The abbreviations used in the accompanying examples are: EGF, epidermal growth factor; RPE, retinal pigment epithelium; TIMP, tissue inhibitor of metalloproteinases; ECM, extracellular matrix; MMP, matrix metalloproteinase; TPA, 12-O-tetradecanoylphorbol-13-acetate; PMSF, phenylmethylsulfonyl fluoride; KLH, keyhole limpet hemocyanin; EDC, 1-ethyl-3(3-dimethylaminopropyl)carbodiimide, APMA, p-aminophenylmercuric acetate; EDTA, ethylenediaminetetraacetic acid; EGTA, ethylene-bis-(oxyethylenenitro)tetraacetic acid.

EXAMPLE I

MMP and TIMP in the Retina

Retina pigment epithelial (RPE) cells, sandwiched between the choroidal blood supply and the neural retina, supply the rods and cones with nutrients and retinol for the visual cycle and remove wastes and the photodamaged membranes shed periodically by these cells. The RPE is responsible for the synthesis and maintenance of portions of the five layers of Bruch's membrane, found at its basal surface on the choroidal side, and much of the interphotoreceptor matrix, found at its apical surface on the photoreceptor side. The regulation of RPE cellular functions is not well understood; the manner of interactive signaling between RPE and adjacent cells and of RPE control of its extracellular matricies is even less certain.

Because of the pivotal role of the RPE and its extracellular matricies in supporting the visual process and the proported complicity of RPE defects in a variety of retinal pathologies, evaluation of the secretion and mRNA levels of these matrix metalloproteinases and TIMP by cultured human RPE cells was undertaken. In addition, we investigated the regulation of these enzymes and their inhibitor by TPA and EGF and identified the EGF receptor, but not EGF, as a product of RPE cells in culture.

Cell Culture and Treatment Methods

Human eyes from donors, which were free from ocular or complicating diseases, were obtained from the Oregon Lion's Eye Bank (Portland, OR). RPE cells were cultured as previously described (49), maintained at 37° C. in an humidified 92.5% air: 7.5% carbon dioxide atmosphere using Dulbecco's modified Eagle media (DMEM), supplemented with 1000 units penicillin, 100 μg fungisone per ml media, and 10% fetal calf serum (all from GIBCO) and used at low passage numbers, generally five. Prior to the initiation of experiments, cells at dense confluence were maintained serum-free with 0.2 mg/ml lactalbumin hydrolysate (OKa, et al.,

*Exp. Cell Res.* 154, 537–547 (1984)) for 48 hours. Where indicated, cultures were exposed to TPA (Sigma) at 100 ng/ml, EGF (source) at 50 ng/ml or vehicle. Human fetal lung fibroblast, IMR-90 (50; American Type Tissue Collection, #CCL186), maintained and used similarly, were also used as indicated.

SDS-PAGE and Substrate Gels

SDS-PAGE was conducted with or without sample reduction (1% betamercaptoethanol). To evaluate proteinase activities, SDS-PAGE substrate gels were polymerized after addition of 0.1% gelatin or 0.1% casein (Sigma) and samples were not reduced or boiled prior to electrophoresis. After electrophoresis, SDS was removed from substrate gels by incubation for 30 min with 2.5% Triton X-100 (Bio-Rad) at 37° C. and proteinase reactions were carried out for 18 hours at 37° C. in buffer containing 150 mM NaCl, 50 mM Tris (pH 8), 10 mM $CaCl_2$ and 1 $\mu M$ $ZnCl_2$ with gentle shaking. Gels were then stained with coomassie blue, destained, dried and photographed. Prestained and unstained molecular weight marker kits (BRL, Bio-Rad or Sigma) were used to estimate the Mr of protein bands.

In the inhibitor studies, PMSF (Boehringer Mannheim) was incubated at 1 mM with the samples prior to electrophoresis and during activity incubations. Metal chelators (10 mM, Sigma) including: 1,10-phenylanthroline, EDTA and EGTA, were included in the SDS/Triton exchange and the proteinase activity incubation buffers. Gels were then processed as detailed above.

Peptides and Antibodies

Fifteen-mer peptides, chosen from regions of human stromelysin, interstitial collagenase, type IV collagenase and TIMP that had minimal sequence homology to each other and to other sequenced proteins, were synthesized and purified by reverse-phase HPLC on a C-18 column or by Multiple Peptide Systems. The peptides were then conjugated to keyhole limpet hemocyanin (Sigma) using 1-ethyl-3(3-dimethylaminopropyl) carbodiimide (Pierce). Polyclonal anti-peptide antibodies were produced in rabbits using MPL/TDM adjuvant (RIBI Immunochem) according to the manufacturer's instructions. The antiserum was tested by ELISA using the KLH-conjugated peptides and by immunoblots of Western transfers from SDS-PAGE gels as described below. Antisera was purified using DEAE-Affi-gel Blue columns (Bio-Rad) and affinity columns with peptide-KLH conjugated coupled to Affi-gel 10 (Bio-Rad) according to the manufacturer's instructions. Polyclonal rabbit antibodies to human skin fibroblast collagenase and TIMP were obtained from local sources and a rabbit polyclonal antibody to human neutrophil gelatinase was produced as described by Hibbs et al., *J. Biol. Chem.* 260, 2493–2500 (1985). Mouse monoclonal antibodies to human EGF and EGF receptor were purchased from Oncogene Science.

Immunoblots of Western Transfers

After traditional SDS-PAGE under reducing conditions, proteins were transferred electrophoretically to nitrocellulose sheets and probed by immunoblot. Second antibody (goat anti-rabbit IgG or horse anti-mouse IgG from Vector) conjugated to alkaline phosphatase was used and blots were developed with the 5-bromo-4-chloro-3-indolyl phosphate/nitroblue tetrazolium substrate system (Kirkegaard & Perry or Sigma) as recommended by the manufacturers. In other studies, the conjugate enzyme was horseradish peroxidase (TAGO) and the substrate was 3,3'-diaminobenzidine tetrahydrochloride (Sigma), also used according to the manufacturer's instructions.

Northern Analysis, Dot Blots and Probes

Stromelysin, type IV collagenase and interstitial collagenase cDNAs were obtained from commercial sources. The cDNAs were amplified in *E. coli*. Probes were retrieved by consecutive restriction cleavage with Bam II and Eco RI, purified on agarose. Radiolabeling of cDNAs was with $^{32}P$-dCTP (NEN/Dupont). Oligonucleotide probes were synthesized by standard techniques and purified by SDS-PAGE. Radiolabling of oligonucleotides was with $^{32}P$-dCTP (NEN/Dupont) using terminal transferase (NEN/Dupont). Northern analysis (Maniatis, et al., *Molecular Cloning: A Laboratory Manual* Cold Springs Harbor, N.Y. (1982)) was conducted in 1% agarose with transfer to Hybond (Amersham) prior to hybridization with radiolabeled cDNA or oligonucleotide probes followed by increasing stringency washes (Davis, et al., *Basic Methods in Molecular Biology*, Elsevier, N.Y. (1986)). Autoradiography was conducted using X-Omat AR5 film (Kodak). A λ phase restriction ladder was run in parallel lanes for apparent Mr determinations. Samples were extracted from confluent control or treated cells. Dot blots using total cellular RNA, which was extracted with NP-40 (Davis, et al., see above) and protein degraded with proteinase K (IBI) or mRNA purified with Oligo dT columns σ were applied to nitrocellulose and hybridized with probes, washed and autoradiographed as discussed above. The DNA content of each test extract was determined and RNA from an equivalent number of cells was then applied to each dot blot, to normalize for possible induction of cell division by treatments.

RESULTS

Basal and TPA-Stimulated Proteinases Activities

The medium from serum-free RPE or IMR-90 cells contains a major gelatinase activity with $Mr \approx 67$ k and caseinase activities with the major activity at $Mr \approx 49$ k, as determined using substrate SDS-PAGE. Incubation with TPA increases the activity observed at these Mr values for both enzymes and in both cell lines; TPA also induces another gelatinase activity at $Mr \approx 92$ k in media from RPE but not in media from IMR-90 cells. IMR-90 and RPE cells both secrete additional gelatinase activity at $Mr \approx 67$ k and caseinase activities with apparent $Mr \approx 55$ k, 52 k, and 44 k, which appear to be degradation and glycosylation variants.

The effects of proteinase inhibitors on these activities in substrate gels allows the identification of all of these activities as metalloproteinases. Trypsin, a serine proteinases added as a control, is inhibited by PMSF, but the gelatinase and caseinase activities are not affected. However, treatment with the metal chelators EDTA, EGTA or 1,10-phenylanthroline completely eliminates secreted RPE cell proteinase but not trypsin activities. Treatment with reducing agents prior to electrophoresis eliminates secreted proteinase activity as detected with either of the substrates.

Immunologic Identification of Proteinases and TIMP(s)

When Western transfers of reducing SDS-PAGE separations of RPE culture media are immunoblotted with specific polyclonal antibodies, collagenase, gelatinase, stromelysin and TIMP are immunolabeled. Collagenase, gelatinase, stromelysin and TIMP (25 k) are observed. TPA-treatment increases the levels of the proteinases and induces new bands, including TIMP at 49 k and TIMP levels are decreased.

Northern Analysis of MMP and TIMP mRNAs

When RNA, extracted from RPE cells after treatment for 8 hours without or with TPA, is electrophoresed and subjected to Northern analysis, individual transcrips of typical sizes are identifiable. The interstitial collagenase cDNA hybridizes with a single transcript at ~2.5 kb, type IV collagenase with one at ~3.1 kb, stromelysin with one at ~2.2 kb and the TIMP oligonucleotide probe hybridizes with one at ~0.9 kb. Similar hybridization is observed with oligonucleotide probes for the metalloproteinases. TPA causes increases in the MMP mRNA levels while decreasing the TIMP mRNA level. The cyclophilin levels are not changed relative to the cellular DNA content, indicating that it may serve as an unstimulated control.

Effects of EGF on mRNA Levels

RNA, extracted from RPE cells at various times after treatment without or with EGF, was treated with proteinase K in the presence of RNase inhibitors and dot blotted onto nitrocellulose. Hybridization with MMP and TIMP probes followed by higher stringency washes and autoradiography, provides temporal information on the individual mRNA levels. All three MMPs show increased transcripts.

Effects of EGF on Secretion of MMPs and TIMP

Similar studies with EGF and NGF in which culture media was removed and analyzed by substrate SDS-PAGE and by immunoblots of Western transfers, show a similar temporal profile for the MMPs and TIMP, although secretion lags behind mRNA level changes.

EGF and EGF Receptor Antibody Studies

Immunohistochemical staining with antibodies to EGF and the EGF receptor show that RPE cells contain high levels of EGF receptor but no detectable EGF. IMR-90 fibroblasts show very light staining for EGF receptor. Western transfers of media and NP-40 extracts of RPE cells show no detectable EGF staining but strong EGF receptor staining at $Mr \approx 180$ k and some smaller degradation products are observed. IMR-90 extracts show less, but detectable EGF receptor. At confluence, RPE cells show reduced levels of EGF receptor. Exposure to EGF also reduces receptor levels while TPA has minimal effects.

EGF and EGF Receptor mRNAs and Down-Regulation

Northern and dot blot analysis of RPE cellular RNA show that RPE cells contain significant levels of EGF receptor but not EGF transcripts. Treatment with EGF clearly reduces EGF receptor mRNA levels with minimal levels occurring by ~24 hours. TPA actually increases receptor transcript levels slightly and no decrease is observed.

DISCUSSION

Cultured human RPE cells secrete interstitial collagenase, type IV collagenase, stromelysin, TIMP (25 k) and an inducable gelatinase (92 k). The combination of methods and probes used and their specific characteristics makes the identification of these proteins relatively certain. Very similar results have been obtained with human and bovine trabecular meshwork cells and explants in culture. Their characteristics, including particularly their Mr values and sequence-specific probe cross-reactivities, suggests that they are all similar or even identical to those expressed by several other cell types. The human fetalung fibroblasts secrete mostly the same forms. The additional forms, mostly apparently due to degradation, glycosylation differences or cleavage-activation, are similar to what is seen with other tissues.

The absence of other proteinase activities in the substrate gels does not eliminate the possibility that other proteinase are present in the media from RPE cultures. The assay conditions that were used show bias against less robust proteinases or those with different substrate specificities.

The mRNAs for the MMPs and TIMP that have been sequenced contain open reading frames for preproenzymes of ~54, 78, and 54 kD. for interstitial collagenase, type IV collagenase and stromelysin, respectively. The TIMP ~0.9 kb mRNA has an open reading frame for a preprotein of 23 kD and runs on SDS-PAGE with an approximate $Mr = 28$ k.

EXAMPLE II

Reducing Intraocular Pressure

Interstitial collagenase is isolated and activated with trypsin, as described by Stricklin et al., *Biochemistry* 22, 61–68 (1983). Stromelysin is prepared and trypsin activated from TPA stimulated rabbit brain capillary endothelial cells, essentially as described by Herron et al., *J. Biol. Chem.* 261, 2810–2813 (1986). A solution of 18 µg/ml each of collagenase and stromelysin in 1 mm $Ca^{++}$ and 0.5 mm $Zn^{++}$ is prepared. Male rabbit intraocular pressure is measured for 5 consecutive days by the procedure of Brubaker, et al., *Invest. Ophthalmol. Vis. Sci.* 27, 1331–1335 (1986), and an average value is established. 25 µl of the above described $MMP/Ca^{++}/Zn^{++}$ solution is injected with a micro syringe into the anterior aqueous chamber. Intraocular pressure is measured for 5 consecutive days, post injection, and averaged. Gonloscopic analysis for inflamation is also conducted. Both techniques indicate reduced intraocular pressure.

EXAMPLE III

Treating Retinal Degeneration

TIMP is prepared from pig synovial cultures by the method of Cawston et al., *Bio. Chem. J.* 195, 159–165 (1981). The pure protein has a $Mr = 28$ kDa based on SDS-PAGE. Rabbits having experimentally induced retinal degeneration are administered, by microinjection, 10 µl of a 30 µg/ml buffered solution of TIMP. The TIMP solution is injected directly into the posterior vitreous each day for 3 days. Retinal degeneration by comparison to controls as measured by light and electron microscopic analysis are conducted at various times post injection. Retinal degeneration is improved in the TIMP injected animals.

We claim:

1. A method for treating open-angle glaucoma in an eye of a subject having glaucoma, comprising:
   providing to the subject's trabecular meshwork or tissue in direct fluid communication therewith, by site specific delivery means, an extracellular matrix metalloproteinase/tissue inhibitor (MMP/TIMP) ratio modulating substance in an effective amount to increase an MMP/TIMP ratio and reduce intraocular pressure, wherein the modulating substance is selected from the group consisting of MMP-1, MMP-2, or MMP-3.

2. The method of claim 1, wherein the site specific delivery means comprises microinjection.

3. The method of claim 1, wherein the modulating substance comprises MMP-1.

4. The method of claim 1, wherein the modulating substance comprises MMP-2.

5. The method of claim 1, wherein the modulating substance comprises MMP-3.

* * * * *